United States Patent [19]

Pearce

[11] Patent Number: 4,632,554
[45] Date of Patent: Dec. 30, 1986

[54] MULTIPLE FREQUENCY LASER INTERFERENCE MICROSCOPE

[75] Inventor: Thomas H. Pearce, Kingston, Canada
[73] Assignee: Queen's University at Kingston, Kingston, Canada
[21] Appl. No.: 558,590
[22] Filed: Dec. 6, 1983
[51] Int. Cl.[4] ............................................. G01B 9/02
[52] U.S. Cl. .................................. 356/349; 356/351; 356/361
[58] Field of Search .............. 356/349, 351, 355, 357, 356/359, 360, 361; 350/505, 510

[56] References Cited

U.S. PATENT DOCUMENTS

| | | | |
|---|---|---|---|
| 2,518,647 | 8/1950 | Teeple et al. | 356/357 |
| 3,359,851 | 12/1967 | Lipschutz et al. | 356/359 |
| 3,914,057 | 10/1975 | Smith et al. | 350/510 X |
| 4,030,831 | 6/1977 | Gowrinathan | 356/351 |
| 4,302,108 | 11/1981 | Timson | 356/359 |

FOREIGN PATENT DOCUMENTS 0003356 1/1978 Japan ................................. 356/349

Primary Examiner—Vincent P. McGraw
Assistant Examiner—S. A. Turner
Attorney, Agent, or Firm—Richard J. Hicks

[57] ABSTRACT

A multiple frequency laser interference microscope in which a source of coherent laser light containing at least two frequencies of light is used in conjunction with a transmitted light polarizing microscope so as to provide an interference microscope. Using a wide fringe mode of operation refractive index becomes directly visible as shades and hues of different colors, and discontinuities and gradients of less than 0.001 may be detected. Using a narrow fringe mode of operation, measurement of fringe shift and thickness permit exact and rapid calculation of refractive index to 0.00n at least.

14 Claims, 10 Drawing Figures

MULTIPLE FREQUENCY LASER INTERFERENCE MICROSCOPE

FIELD OF INVENTION

This invention relates to interferometers and more particularly to multiple frequency laser interference microscopy.

DISCUSSION OF PRIOR ART

The phenomenon of interference has, of course, long been recognized as one of the most effective means for determining refractive indices, phase differences, light source wave lengths and the like and for making distance measurements. Numerous interferometers have been described in the literature, including signal frequency laser interferometers (vide, for example, Canadian Patent No. 833,877 issued Feb. 10, 1970 to Erickson) which have been developed to take advantage of the unprecedented spectral purity and coherence of laser light. It has now been found that significant improvements over single frequency laser interferometers can be achieved in the access of refractive index measurement dispersion of refractive index, and refractive index gradients among others, using a multiple frequency laser interferometer. Using the techniques of the present invention accuracies of an order of magnitude greater than heretofore possible may be achieved.

It is axiomatic in interference studies that light of one frequency cannot produce interference effects with light of another frequency. It follows therefore, that, with mixed light, each frequency of light behaves as though the other were not there. Thus, if pure red, green and blue light frequencies are mixed and caused to interfere, it would be logical to expect the resulting interferogram to consist only of these colours in various intensities. As will be demonstrated in more detail hereinafter, this has been found not to be the case. In the case of red and green light, for example, vivid shades of yellow and other colours are observed in the interferogram, but are not, of course, present in the spectrum which still only has red and green. The explanation of this somewhat unexpected result lies in the difference between frequency and wavelength on the one hand, and colour, on the other. Colour is that which is perceived by the human eye - frequency is that which is actually present in the spectrum. Colour vision in the eye and colour in photographic film is the result of combinations of the three primary colours, red, green and blue. For example, the eye has no way of determining yellow light directly but relies on two receptors which are sensitive to red and green. Thus, in the interferogram, red and green light together are perceived as yellow. This colour effect has been found to be very useful for detecting and dramatically emphasizing slight variations in optical path in many practical situations ranging from biological studies of cell tissues to geological studies of mineralogical and petrological specimens.

OBJECT OF INVENTION

It is, therefore, an object of the present invention to provide a multi-frequency laser interferometer useful in determining refractive indices and the like.

Another object of the invention is to provide an improved method of optical interferometric determinations using a multi-frequency laser beam as the light course.

BRIEF SUMMARY OF INVENTION

Thus by one aspect of this invention there is provided an interferometer comprising:

(a) a first laser light source to provide a polarized coherent light beam of a first selected frequency;

(b) a second laser light source to provide a coherent light beam of a second selected frequency differing from said first selected frequency and parallel polarized relative to said beam from said first laser light source;

(c) means to combine beams from said first and second sources into a single beam of mixed said frequencies;

(d) first optical means to divide said single beam into a reference beam and a sample beam;

(e) second optical means to recombine said reference beam and said sample beam so as to cause interference therebetween and produce an interferogram;

(f) a first optical path between said first and second optical means for passage therealong of said reference beam;

(g) a second optical path, between said first and second optical means for passage therealong of said sample beam;

(h) means to interpose a sample at a selected position in said second optical path; and (i) means to scan said interferogram.

By another aspect of this invention there is provided in a method for making optical determinations by laser interferometry the improvement comprising:

providing a beam of coherent laser light containing at least two parallel polarized selected frequencies, splitting said beam into a sample beam which passes through a stationary sample under detemrination and a reference beam which bypasses said sample, causing said sample beam and said reference beam to interfere so as to produce an interferogram containing more colours than there are frequencies in said beam.

DESCRIPTION OF DRAWINGS

The invention will be described in more detail hereinafter with reference to the drawings in which:

FIG. 5 (*b*) is an interferogram of the same pehnocryst as in FIG. 5 (*a*), with the optical tuner adjusted to give red and green interference colours.

DETAILED DESCRIPTION

In order to determine refractive index by interferometry, the difference in the optical path between a known and an unknown material is determined and compared to a reference beam of fixed, but adjustable optical path. Optical path (OP) is defined as the product of refractive index (N) and the thickness (t) thus:

$$OP = Nt$$

If the number of wavelengths in the optical path is M, then $$OP = ML_o$$

where $L_o$ is the wavelength in vacuo of the light used. For two different optical paths due to different refractive indicies:

$$OP_1 - OP_2 = (M_1 - M_2)L_o$$

The difference in the number of wavelengths is referred to as the shift, S ($S = M_1 - M_2$) and is the fundamental observation.

The known material acts as an internal standard to permit an absolute measurement of refractive index. The interference effect which is measured is, of course, due to the difference in optical path between the sample and reference beams. These measurements may be made using either a "narrow" or "wide" fringe technique.

Figure 2A:
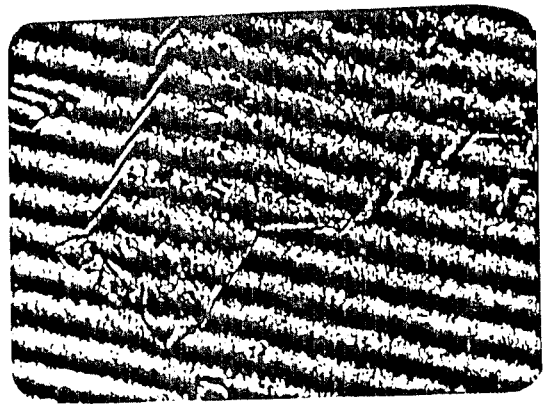
FIGS. 2 (*a*), (*b*) and (*c*) are interferograms of a thin section of a grain of anorthite mounted in Canada balsam using green, red and blue laser light respectively.
Figure 2B:
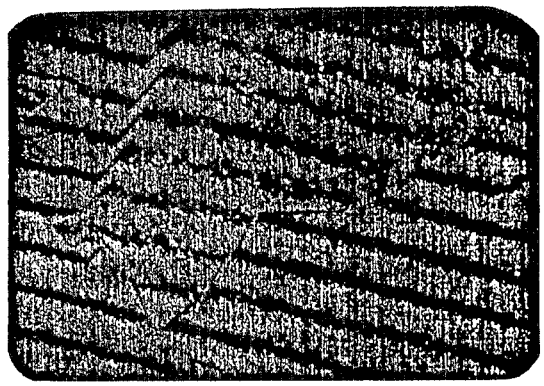
Figure 2C:
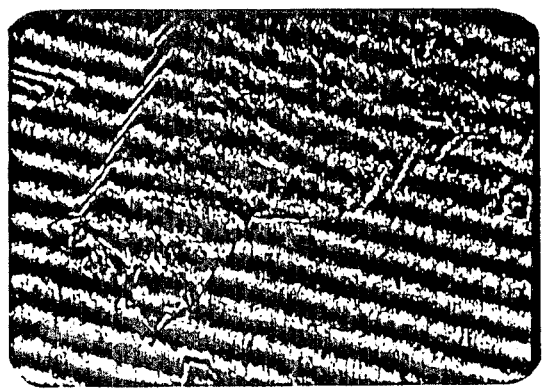
Figure 3A:
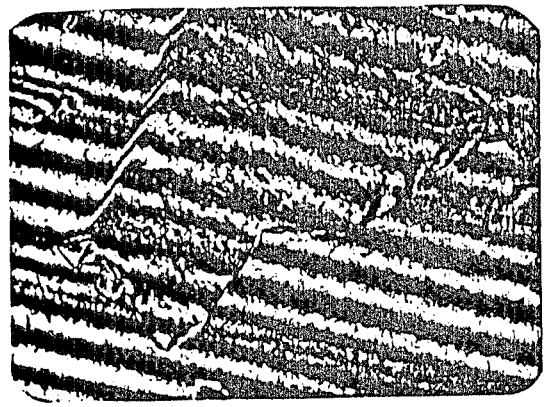
FIGS. 3 (*a*) and (*b*) are interferograms of the same grain of anorthite used in FIG. 2 using green/red and red/blue laser light respectively.
Figure 3B:
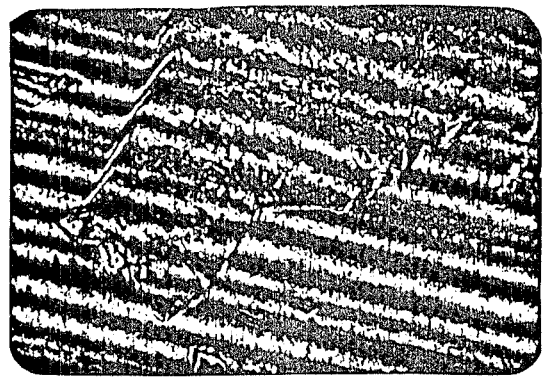
Figure 4:
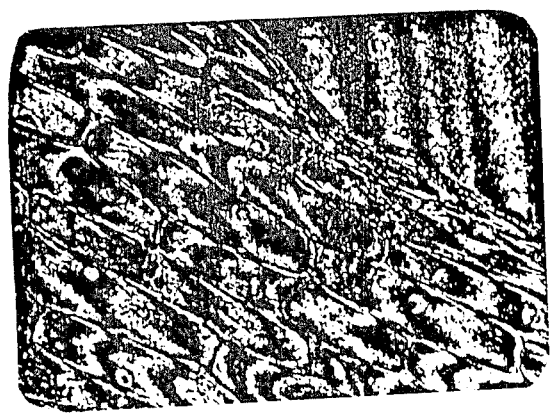
FIG. 4 is a narrow fringe interferogram of onion skin cells mounted in water using green/red laser light.

In the "narrow fringe" method, the interference fringes are adjusted to be significantly smaller than the object being observed, as in FIGS. 2, 3 and 4. The order of interference for each fringe at any point is determined by the optical path difference between the sample beam and the reference beam. The interferogram in such a case appears to be a series of coloured and dark stripes which are offset at discontinuities and curved at smooth gradients of RI. From the above equations, if $N_1$ is the RI of a known material in contact with an unknown of $RI = N_2$, then in general the fringes in an interferogram will be shifted at the boundary according to the relationship:

$$N_1 - N_2 = S L_o/t$$

where S is the observed shift in apparent wavelength in the interference pattern, $L_o$ is the wavelength in vacuo of the light used, and t is the thickness (in the same units as the wavelength, of course). This is the fundamental equation governing interferometric observations. If more than one colour of light is present then each colour behaves as if the others are not present. The resulting interference pattern is the sum of the individual patterns for each energy of light present.

In particular, note that an accurate RI determination is tied to an accurate thickness measurement as well as the shift determination. In principle, thickness measurements can be determined quite accurately in cases where both refractive indices are known. It is useful to note that, because of the form of the equation, if $(N_1 - N_2)$ is small, then a rather large error in the thickness may be tolerated with acceptable accuracy in the RI determination. This is important because it is difficult to measure the thickness of a microscopic particle with better than 1 or 2% accuracy. Even this error is entirely consistent with an overall error in RI of 0.00n. Table II represents data for an actual calculation of the RI of a known sample of optical glass, using a grain mount in thermoplastic, the "quick method" of preparing material for analysis.

TABLE I

| COLOUR | LASER LINES WAVELENGTH | POWER | LASER |
|---|---|---|---|
| Red | 632.82 nm | (2 mw) | Helium-Neon |
| Green | 514.532 nm | (9 mw) | Argon-Ion |
| Blue-Green | 487.986 nm | (15 mw) | Argon-Ion |
| Blue-I | 476.486 nm | (2 mw) | Argon-Ion |
| Blue-II | 457.935 nm | (1 mw) | Argon-Ion |

Reference: Handbook of Tables for Applied Engineering Science, 2nd Edition, 1976, Boltz, R. E., and Tuve, G. L., editors. CRC Press, Cleveland, Ohio. Tables 2-68 and 2-69.

TABLE II

| | SAMPLE CALCULATION | | | RAPID GRAIN MOUNT METHOD | |
|---|---|---|---|---|---|
| | Standard Medium | Optical Glass | $\Delta N$ | N (calc) | Error |
| A | 1.65574 | 1.55740 | 0.09834 | 1.55828 | 0.00088 |
| B | 1.67591 | 1.56800 | 0.10791 | 1.56568 | 0.00231 |

For a single determination of a grain of 48.7 micron thickness and shift as indicated. Cargile optical glass standard in thermoplastic.
A = Red light, 632.8 nm He—Ne Laser shift, S = 7.5 fringes
B = Blue-green light, 488.0 Argon-Ion Laser, S = 11.0 fringes In the "wide fringe" method the optics are aligned as precisely as possible, so that the centre of "zeroth" fringe becomes very wide (ideally, filling the entire field of view). All other things being equal, the only differences in the optical path will be due to variations of RI within the sample itself. The resulting interferogram now has the appearance of a "normal" image. It is a "picture" of the objects in the field of view colour-contoured with respect to optical path (FIGS. 5 (a) and (b) and FIG. 6). The interferogram may, therefore, be treated as though it were a topographic map in which refractive index differences are contoured (optical "height" instead of geographic height). Since refractive index is directly visible, all optical discontinuities and gradients become visible often with startling visual effects. It is possible to estimate the actual refractive index gradients by observing the interference colour, although the fraction of a fringe shift is, in general, difficult to determine. The use of more than one colour of light makes it relatively easy to distinguish positive from negative gradients in refractive index.

This is not possible with a single laser frequency and is one of the principal advantages of the use of multiple laser frequencies according to the present invention.

It will be appreciated that any feature which affects the refractive index becomes visible. Thus chemical composition, structural or crystallographic state may become directly visible. Such effects may be seen whether due to intrinsic properties of the specimen (chemistry) or its history of treatment (i.e. stress effects). If the relationship between refractive index and chemical composition in naturally occurring mineral solid solutions is considered, for example, the variation in chemical composition necessary to yield an observable optical effect may be determined. Table III below illustrates some minimal compositional variations which can be readily detected by the wide fringe method. In some cases, such as garnets (isotropic) and nepheline (uniaxial) only a method such as interferometry is capable of rendering optical zonation visible.

TABLE III

| MINIMUM VISIBLE ZONING IN MINERALS WIDE FRINGE TECHNIQUE | |
|---|---|
| MINERAL SERIES | MOLE % FOR 0.001 N |
| Olivine | 0.5% |

TABLE III-continued

MINIMUM VISIBLE ZONING IN MINERALS WIDE FRINGE TECHNIQUE

| MINERAL SERIES | MOLE % FOR 0.001 N |
| --- | --- |
| Garnet series | 0.5% to 1% |
| Enstatite-hypersthene | 0.8% |
| Hornblende | 1% |
| Scapolite (Meionite) | 1.1% |
| Aegirine-Augite | 1.4% |
| Actinolite-Termolite | 1.5% |
| Plagioclase | 2% |
| Nepheline-kaliophilite | 3% |
| Sanidine | 10% |

Note:
The above Table gives the approximate chemical composition corresponding to 0.001 gradient in refractive index for the mineral series indicated. Data from various sources.

Figure 1:
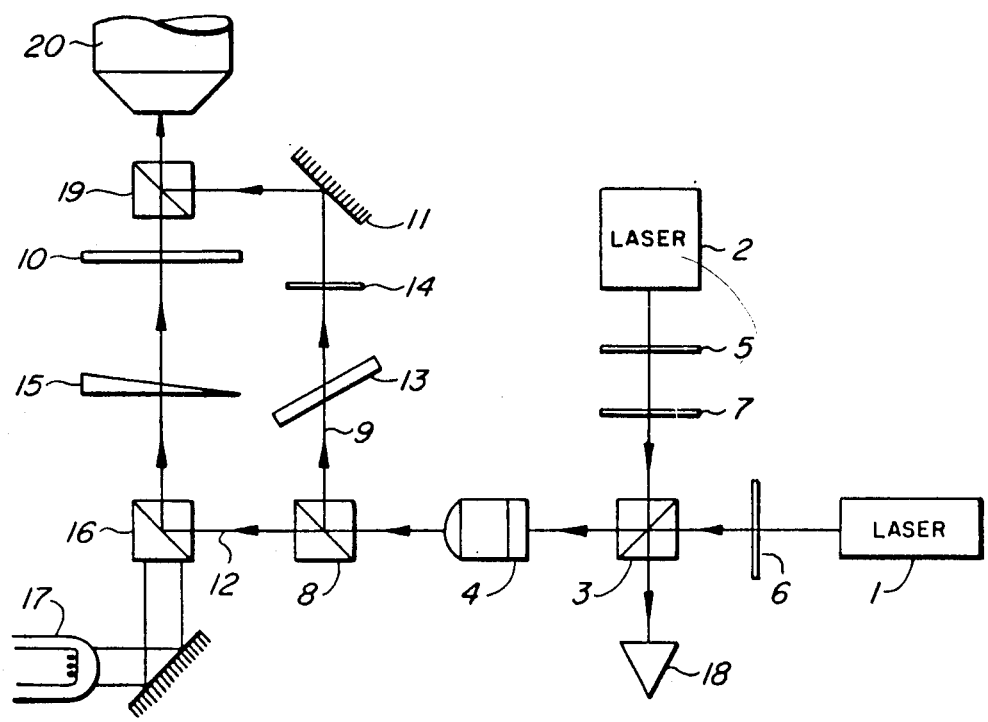
FIG. 1 is a schematic representation of an interferometer according to one embodiment of the invention.

An apparatus specifically adapted to carry out either of the above discussed methods is illustrated schematically in FIG. 1. Light beams from two lasers 1, 2 are combined in a beam splitter 3 to produce a single beam of mixed frequency mixed coherent light. Laser 1 is a Helium-Neon 2 m watt laser which only lases in the red producing the well known 632.8 nm line, and laser 2 is a tunable Argon-Ion 20m watt laser which produces several lines in the visible green and blue region as illustrated in Table 1 above. The single mixed frequency beam then passes through a beam expander 4. Within this beam of light each frequency is coherent but the different frequenices are not mutually coherent. The power output of laser 2 is controlled by its power source and this is a convenient method of balancing the output of the two lasers to produce a mixed light which, in an interferogram, actually contains more colours than there are frequencies of light. Additional balance and intensity control is provided by blue/green balance filter 5 and variable density filters 6,7. The light from both lasers 1,2 is polarized and the lasers must therefore be oriented so that the polarization directions are coincident when the mixed beam leaves the source beam splitter 3.

The beam of mixed light then enters the second part of the apparatus namely a modified Mach-Zehnder interferometer attached to a polarizing microscope. A beam splitter 8 separates the light into a reference beam 9 which bypasses the the sample 10 entirely via a first surface mirror 11, and a sample beam 12 which passes through the sample and contains phase information of interest. The reference beam 9 may be "tuned", that is, slightly changed in its optical path, by means of a tilting compensator 13, sometimes referred to as an optical tuner, and further adjusted by one or more filters 14. Various filters and compensators, such as a wedge compensator 15, may be provided in the path of beam 12 for adjustment of the interference pattern. A beam splitter 16 is also desirable so that the sample 10 may be viewed either by way of laser beam 12 or by normal white light from a white light source 17. A beam dump 18 may also be provided. The phase information contained in sample beam 12 is only visible as interference fringes where the reference beam 9 interferes with the sample beam 12 when combined in beam splitter 19 to produce the interferogram which may be scanned or observed and/or photographed through microscope 20, in conventional manner. The interferogram is composed of fringes of equal interference order (optical path difference, in this case) and is not, therefore, an image in the strict sense of the term. In the wide fringe mode of operation, however, the interferogram is virtually indistinguishable from an image but for correct interpretation requires the knowledge that it is, in fact, an interferogram.

Figure 5A:
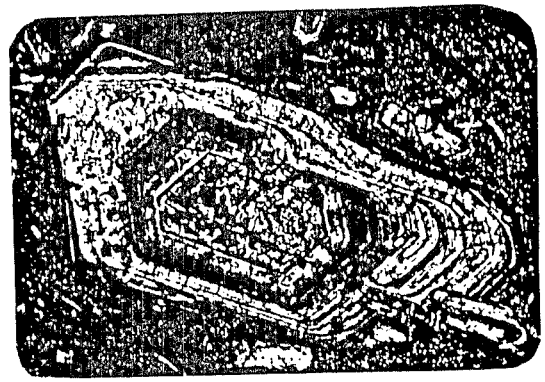
FIG. 5 (*a*) is a wide fringe interferogram of a plagioclase phenocryst from a Mt. St. Helens andesite using green/red laser light.
Figure 5B:
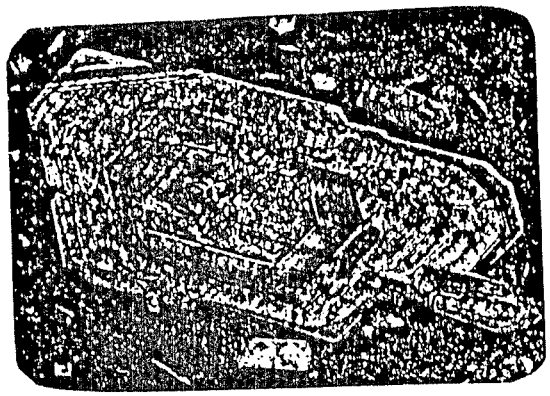
Figure 6:
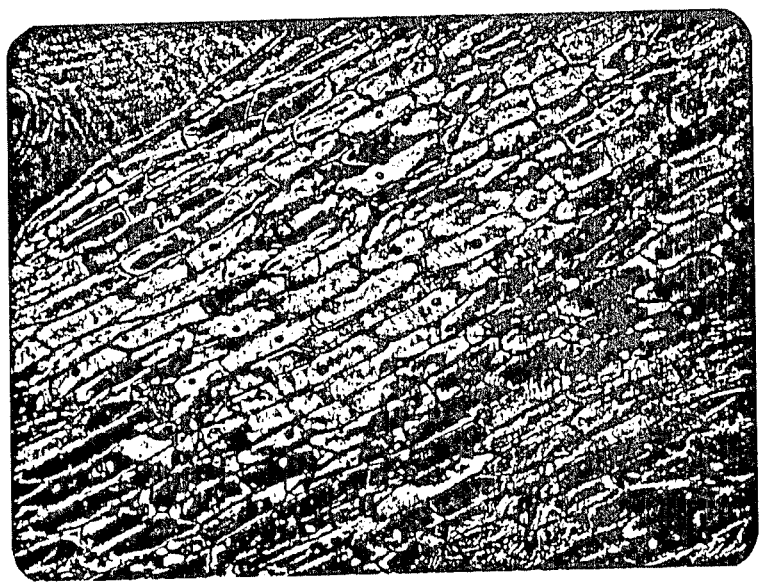
FIG. 6 is a wide fringe interferogram of onion skin cells mounted in water using green/red laser light.

With the narrow fringe technique, as described hereinabove, diagnostic studies of single particles (see FIGS. 2 (a), 2 (b) 2 (c), 3 (a) and 3 (b)), fibers and biological materials (FIG. 4), are readily possible. Using grain mounts, refractive index may be determined to 0.00 n on a routine basis for particles as small as 20 microns. It should be noted that only a single particle is needed for this determination. Using the wide fringe technique, as hereinbefore described, striking visual results are achieved with both geological and biological specimens. FIGS. 5 (a) and 5 (b) illustrate a plagioclase phenocryst from Mt. St. Helens, Washington (probably not from the eruption of May 18, 1980) and attention is particularly drawn to the wealth of fine detail visible. The finest zones in the plagioclase are only 5 microns wide, each colour of zone represents a different refractive index and hence a different composition of plagioclase. The history of growth of the plagioclase is recorded in these Figures. The onion cells in FIG. 6 are only about 0.5 mm long and the cell nuclei and other features are clearly visible. Note that the same cells viewed by the narrow fringe technique (FIG. 4) do not show the nuclei nearly as clearly. Because the eye (and photographic film) is extremely sensitive to slight changes in colour, refractive index gradients corresponding to an optical path difference of at least 1/20 of a wavelength are readily visible. This corresponds to a refractive index gradient of 0.001 for a 30 micron thick sample or 0.0001 for a 3 micron thick sample.

The use of lasers as the light source in the arrangement of the present invention is considered an essential feature of the invention not only for their narrow emission lines but also because of their coherence which makes interference possible over large distances. Because of this, the actual optical paths and the magnitude of the optical path differences are not critical and this, in turn, relaxes design criteria for the optics of the interferometer, and enables the use of relatively inexpensive standard components.

I claim:
1. An interferometer comprising:
    (a) a first laser light source to provide a polarized coherent light beam of a first selected frequency;
    (b) a second laser light source to provide a coherent light beam of a second selected frequency differing from said first selected frequency and parallel polarized relative to said beam from said first laser light source;
    (c) means to combine beams from said first and second sources into a single beam of mixed said frequencies;
    (d) first optical means to divide said single beam into a reference beam and a sample beam;
    (e) second optical means to recombine said reference beam and said sample beam so as to cause interference therebetween and produce an interferogram;
    (f) a first optical path between said first and second optical means for passage therealong of said reference beam;
    (g) a second optical path, between said first and second optical means for passage therealong of said sample beam;
    (h) means to interpose a sample at a selected position in said second optical path immediately adjacent said second optical means; and

(i) optical microscope means to scan said interferogram.

2. An interferometer as claimed in claim 1 including single camera means to photograph said interferogram.

3. An interferometer as claimed in claim 1 wherein said first light source comprises a helium-neon laser and said second light source comprises an argon-ion laser.

4. An interferometer as claimed in claim 1 wherein said second light source is an argon-ion laser producing a line having a wavelength selected from 514.532 nm, 487.986 nm, 476.486 nm and 457.935 nm.

5. An interferometer as claimed in claim 1 including compensator means in at least one of said first and second optical paths.

6. An interferometer as claimed in claim 1 including beam splitter means arranged to introduce light from an external source into said second optical path whereby said sample may be scanned in said light from said external source.

7. In a method for making optical determinations by laser interferometry the improvement comprising:
providing a beam of coherent laser light containing at least two parallel polarized selected frequencies, splitting said beam into a sample beam which passes through a stationary sample under determination and a reference beam which bypasses said sample, causing said sample beam and said reference beam to interfere so as to produce an interferogram containing more colours than there are frequencies in said beam.

8. A method as claimed in claim 7 wherein interference fringes contained in said interferogram are adjusted to be significantly narrower than the sample being observed.

9. A method as claimed in claim 8 wherein said optical determination comprises measurement of refractive index in said sample.

10. A method as claimed in claim 7 wherein a central interference fringe in said interferogram is adjusted to substantially fill a field of view.

11. A method as claimed in claim 10 wherein said optical determination is selected from determination of optical thickness of a sample in a selected colour of light and determination of refractive index variation in a sample.

12. A method as claimed in claim 11 wherein said sample is a geological specimen containing crystal zoning.

13. A method as claimed in claim 11 wherein said sample is a biological specimen having a structure to be determined.

14. A method as claimed in claim 7 wherein said laser beam comprises a helium-neon laser and an argon-ion laser.

* * * * *